US00PP21608P2

(12) United States Plant Patent
Kazimier

(10) Patent No.: US PP21,608 P2
(45) Date of Patent: Jan. 4, 2011

(54) LACEBARK ELM TREE NAMED 'MON1'

(50) Latin Name: *Ulmus parvifolia*
Varietal Denomination: MON1

(76) Inventor: Kenneth K. Kazimier, 5214 W. Nippersink Dr., Richmond, IL (US) 60071

( * ) Notice: Subject to any disclaimer, the term of this patent is extended or adjusted under 35 U.S.C. 154(b) by 5 days.

(21) Appl. No.: 12/462,369

(22) Filed: Aug. 3, 2009

(51) Int. Cl.
*A01H 5/00* (2006.01)

(52) U.S. Cl. ..... Plt./221

(58) Field of Classification Search ..... Plt./221
See application file for complete search history.

(56) References Cited

U.S. PATENT DOCUMENTS

PP10,846 P * 3/1999 Cully ..... Plt./221
PP16,883 P3 * 7/2006 Whitcomb ..... Plt./221

* cited by examiner

*Primary Examiner*—Wendy C. Haas
(74) *Attorney, Agent, or Firm*—Penny J. Aguirre

(57) ABSTRACT

A new cultivar of *Ulmus parvifolia*, 'MON1', characterized by its uniform upright plant habit developing to an oval form at maturity and its hardiness at least to U.S.D.A. Zone 4b.

2 Drawing Sheets

Botanical classification: *Ulmus parvifolia.*
Variety denomination: 'MON1'.

BACKGROUND OF THE INVENTION

The present invention relates to a new and distinct cultivar of *Ulmus parvifolia*, and will be referred to hereafter by its cultivar name, 'MON1'. 'MON1' is a new cultivar of lacebark elm or Chinese elm, a deciduous tree grown for use as a landscape plant.

The new *Ulmus* was discovered as a single unique naturally occurring whole plant mutation of *Ulmus parvifolia* as a 2-inch B & B tree in the Inventor's nursery in fall of 1992 in Spring Grove, Ill.

Asexual reproduction of the new cultivar was first accomplished by the Inventor by softwood cuttings in the summer of 1996 in Spring Grove, Ill. The characteristics of this cultivar have been determined to be stable and are reproduced true to type in successive generations.

SUMMARY OF THE INVENTION

The following traits have been repeatedly observed and represent the characteristics of the new cultivar as observed for 16 years in Spring Grove, Ill. These attributes in combination distinguish 'MON1' as a unique cultivar of *Ulmus parvifolia.*

1. 'MON1' exhibits a uniform upright growth habit developing an oval shape on maturity.
2. 'MON1' exhibits cold hardiness at least to U.S.D.A. Zone 4b.

In comparison to the parent plant, *Ulmus parvifolia*, 'MON1' has an upright habit, whereas *Ulmus parvifolia* has an open and variable plant habit. 'MON1' can also be most closely compared to *Ulmus parvifolia* cultivars 'Zettler' (U.S. Plant Pat. No. 10,846) and 'Whit XXX' (U.S. Plant Pat. No. 16,883). Both cultivars are similar in developing upright and oval plant habits, however 'MON1' differs in showing better winter hardiness as both cultivars are cold hardy to U.S.D.A Zone 5.

BRIEF DESCRIPTION OF THE DRAWING

The accompanying colored photographs of 'MON1' illustrate the overall appearance and distinct characteristics of the new *Ulmus parvifolia*. The photographs were taken of a plant sixteen years in age as grown outdoors in Spring Grove, Ill.

Figure 1:
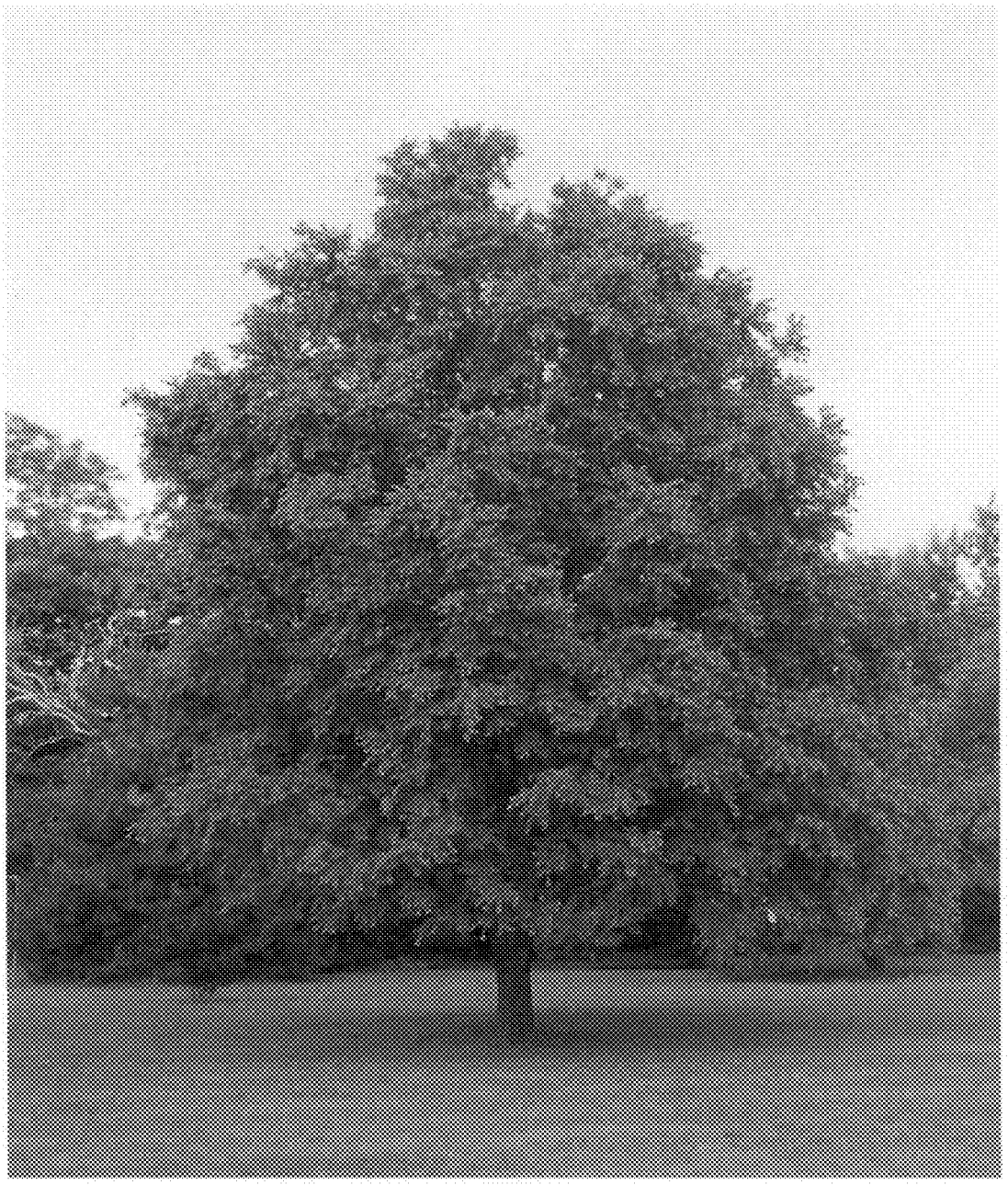
FIG. 1 illustrates the overall plant habit in summer.
Figure 2:
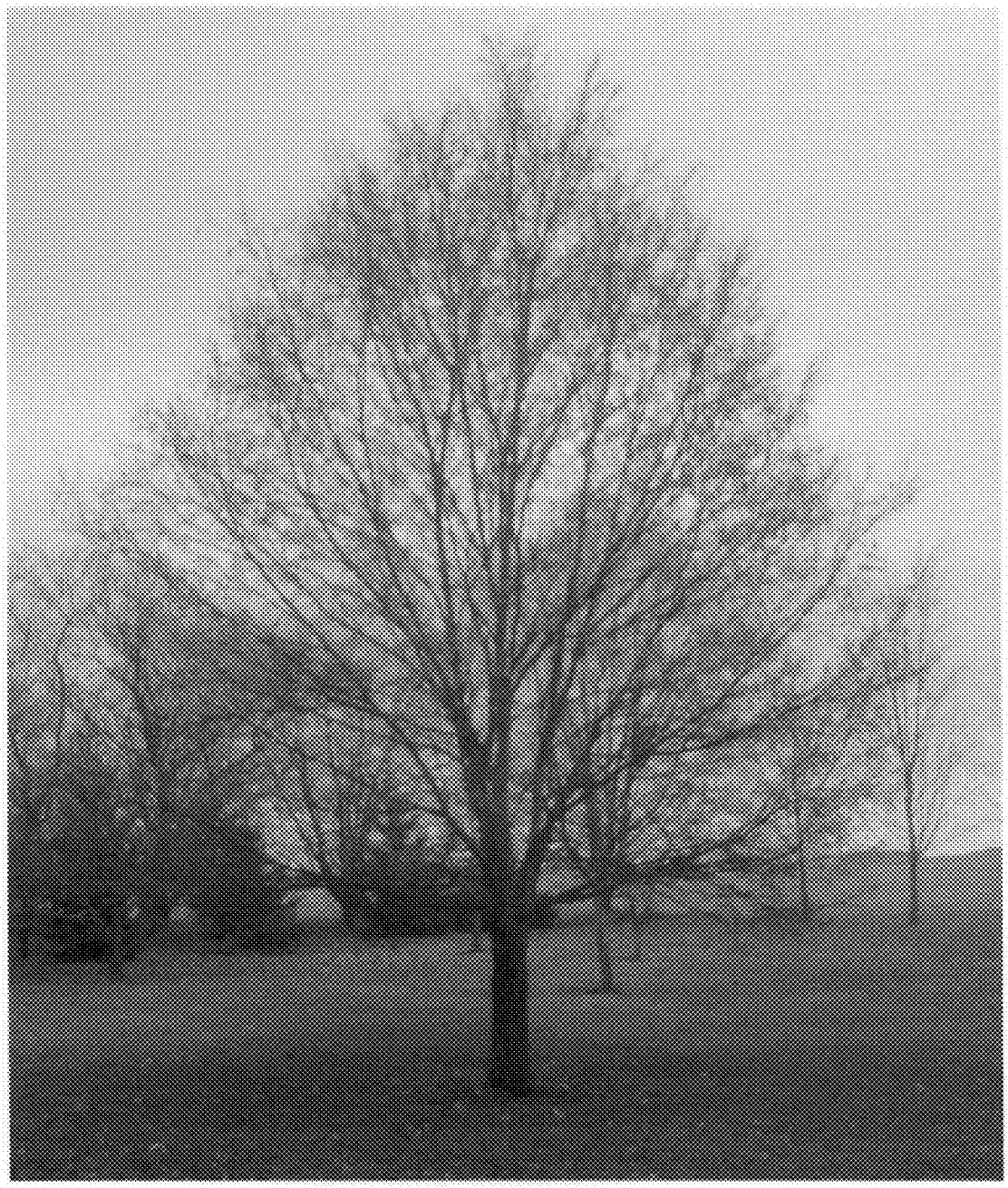
FIG. 2 provides a view of 'MON1' in winter and shows the overall plant structure without foliage.

The colors in the photographs may differ slightly from the color values cited in the detailed botanical description, which accurately describe the colors of the new *Ulmus parvifolia.*

DETAILED BOTANICAL DESCRIPTION

The following is a description of the new cultivar as grown outdoors and observed for sixteen years in Spring Grove, Ill. The detailed botanical data was collected on a three year-old plant of 'MON1' that was grown in a 10-gallon container in New Hope, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Botanical classification.*—'MON1' is a cultivar of *Ulmus parvifolia.*

*Parentage.*—Naturally occurring seedling selection of *Ulmus parvifolia.*

*Plant habit.*—Deciduous tree with a uniform, upright and oval habit.

*Height and spread.*—Reaches about 2.5 m feet in height and 5 feet in width (three year-old plant), reaches about 10.5 m (35 ft) in height and about 4.5 m in width (15 ft) in sixteen years.

*Cold hardiness.*—At least in U.S.D.A. Zones 4 to 9.

*Diseases and pests.*—No apparent disease problems have been observed to date.

*Root description.*—Fibrous, freely branched.

Growth and propagation:

*Propagation.*—Softwood cuttings and T-bud grafting.

*Time required for graft development.*—About 4 weeks to develop in a 36-cell tree pot.

*Growth rate.*—Moderate.

Stem description:

*Shape.*—Round to slightly oval.

*Stem color.*—Main trunk and secondary branches (bark) blend of 97A and 97C, with lenticels 164A in color about 6 per 2 square centimeters, new growth; a blend of 199B and 199C.

*Branching.*—Irregular but primarily alternate, internode length for secondary branches is an average of 2.5 cm.

*Stem size.*—Main trunk; about 1 cm in diameter (15 cm from base) and 2.5 m in length, secondary branches; an average of 5 mm in diameter and 1 m in length, and tertiary branches; an average of 3 mm in diameter and 50 cm in length.

*Stem surface.*—New growth is smooth with areas of pubescence, mature bark has vertical striations and is somewhat glaucous.

Foliage description:

*Leaf shape.*—Elliptic to obovate.

*Leaf division.*—Simple.

*Leaf aspect.*—Held nearly horizontally to slightly pendant stem.

*Leaf base.*—Oblique.

*Leaf apex.*—Broadly acute.

*Leaf fragrance.*—None.

*Leaf venation.*—Pinnate, 137C in color on upper surface, 138C on lower surface with 145C midrib.

*Leaf margins.*—Serrated.

*Leaf arrangement.*—Alternate with terminal leaves on branch larger.

*Leaf internode length.*—An average of 5 mm.

*Leaf attachment.*—Petiolate.

*Leaf surface.*—Glabrous on upper surface and finely puberulent on lower surface.

*Leaf size.*—Mature to about 4.6 cm in length and 2.3 cm in width.

*Leaf color.*—Mature growth; Upper surface; 137B, lower surface; a color between 147B and 147C, new growth; upper and lower surface 146B.

*Petioles.*—An average of 3 mm in length and 1 mm in width, color is 146B, surface is pubescent.

Flower description:

*Flowers.*—Typical for the species, characterized as inconspicuous and occurring in early fall in Illinois.

*Seed.*—Seed production has not been observed, fruit production is generally sparse for the species.

It is claimed:

1. A new and distinct cultivar of lacebark elm tree named 'MON1' as herein illustrated and described.

* * * * *